United States Patent [19]

Albanchez Matiaci et al.

[11] Patent Number: 5,176,519
[45] Date of Patent: Jan. 5, 1993

[54] PROCEDURE FOR A VISUAL AND MICROSCOPIC STUDY OF THE CHARACTERISTICS OF A VEGETABLE PLANT

[76] Inventors: Angeles Albanchez Matiaci; Jose M. Fernandez Garcia, both of Mayor, 90, 02440 Molinicos (Albacete), Spain

[21] Appl. No.: 857,453

[22] Filed: Mar. 25, 1992

[30] Foreign Application Priority Data

Mar. 26, 1991 [ES] Spain .................................. 9100816

[51] Int. Cl.$^5$ .............................................. G09B 23/00
[52] U.S. Cl. ..................................... 434/295; 434/296
[58] Field of Search ............................... 434/295-297

[56] References Cited

U.S. PATENT DOCUMENTS

| | | | |
|---|---|---|---|
| 472,980 | 4/1892 | Brown | 434/297 |
| 792,501 | 6/1905 | Davis | 434/297 |
| 891,971 | 6/1908 | Bade et al. | 434/297 |
| 1,204,723 | 11/1916 | White | 434/297 X |
| 1,554,641 | 9/1925 | Miner | 434/295 X |
| 1,949,268 | 2/1934 | Clark | 434/297 X |
| 3,298,881 | 1/1967 | Higley et al. | 434/296 X |
| 4,723,914 | 2/1988 | Tachibana | 434/297 |

*Primary Examiner*—Gene Mancene
*Assistant Examiner*—L. Thomas
*Attorney, Agent, or Firm*—Wigman & Cohen

[57] ABSTRACT

Procedure for the visual and microscopic study of the characteristics of a vegetable plant; characterized because it includes the stages of: collection and selection of specific leaves from the plant; submission of a leaf to a pressing operation at approximately 6 kg/cm$^2$ and later drying at ambient temperature of approximately 30°; under these conditions the leaf undergoes soaking in a disinfectant solution; thereafter the leaf is placed between two plastic sheets or films and these are closed with sterilization at 125° C. which temperature is appropriate to carry out the thermowelding which takes place at a pressure of 6 kg/cm$^2$ to remove any possible air bubbles.

5 Claims, 1 Drawing Sheet

PROCEDURE FOR A VISUAL AND MICROSCOPIC STUDY OF THE CHARACTERISTICS OF A VEGETABLE PLANT

BACKGROUND OF THE INVENTION

1. Field of the Invention

The invention refers to a procedure for the visual and microscopic study of the characteristics of a vegetable, such as: its diseases, flora identification, plates, nutrition organs, reproduction system, etc.

2. Description of the Prior Art

Currently the study of these characteristics is carried out using photographs, films and other similar representations.

Obviously this system is deficient with regard to identification of plants since the film or photograph is not accompanied by the visual characteristics of the plant in question.

Using the system of photography and/or film it is impossible to study diseases of deciduous plants because they cannot be obtained in optimum study conditions once they have fallen from the tree.

With the procedure of the invention, these above mentioned problems are resolved since the characteristics of a vegetable plant can be studied and visualized microscopically under really optimum obervation conditions that, in turn, allows a sample to be made available for a very long period of time.

SUMMARY OF THE INVENTION

Furthermore, the manner of presentation and preservation allows the observer or examiner to keep the sample without danger of its deterioration or loss.

According to the invention, the procedure includes the stages of:

Collection and selection of specific leaves from the plant.

Subjecting a leaf to a drying operation at ambient temperature of approximately 30° and later, when the leaf is dry, it is placed under a pressure of approximately 6 kg/cm$^2$.

The leaf in these conditions is subjected to soaking in a disinfecting solution.

The leaf is placed between two plastic films and closed with sterilization at 125° C., which temperature is appropriate for carrying out thermo-welding.

The thermo-welding is carried out at a pressure of approximately 6 kg/cm$^2$ so that any possible air bubbles will disappear.

Also enclosed with the plant is a piece of paper or cardboard bearing the characteristics of the plant, its applications and a drawing of the same.

With the procedure of the invention, the leaf may be studied simply and securely, and also offers a means of studying the various constituent parts of the plant in schools or research centres.

The plastic-covered leaf retains optimum conditions for study.

The presentation may be on index cards or on folio type sheets that can be bound to form a book with the specifications.

Given below is an example of how the procedure of the invention is carried out, with this example being merely an explanation that in no case limits the invention, all as shown in the attached drawings, in which:

DETAILED DESCRIPTION OF THE INVENTION

Figure 1:
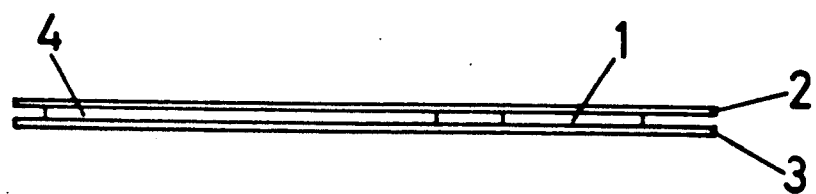
FIG. 1 shows a side view of the placing of a plant leaf between two sheets of plastic film.
Figure 2:
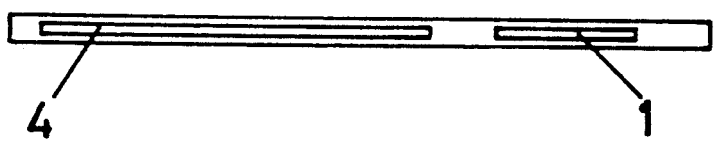
FIG. 2 shows a similar view to that of FIG. 1, when the closure of the leaf has been made.
Figure 3:
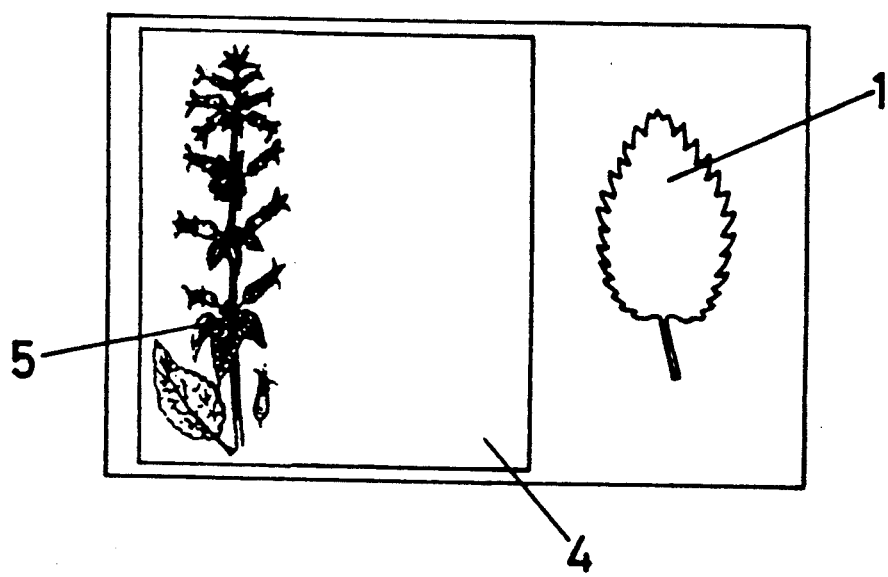
FIG. 3 shows a front view of FIG. 2.

Following the stages of the procedure of the invention, the leaf 1 is taken and pressed at 6 kg/cm$^2$ and dried at ambient temperature.

Before placing it between the two pieces of plastic film 2 and 3, it is soaked in a disinfectant solution, sterilized at a temperature of 125° C. at which temperature the plastic sheets are closed by thermo-welding under a pressure of 6 kg/cm$^2$ to remove any possible air bubbles.

With the leaf a piece of card 4 of appropriate size is included, on which is printed a drawing of the plant 5 and also the characteristics of the plant are specified.

Having sufficiently described the nature of the invention and the manner in which it is put into practice, it should be noted that the layouts described above and represented by the attached drawings, may be modified in detail provided the fundamental principle is not altered.

What is claimed is:

1. A process for the visual and microscopic study of a plant comprising the steps of:
    selecting a leaf from the plant;
    pressing the leaf at a pressure of approximately 6 kg/cm$^2$;
    drying the leaf at a temperature of approximately 30° C.;
    placing the leaf in a bath of disinfectant; and
    placing the leaf between two plastic sheets and sealing the sheets together at a temperature of approximately 125° C. and a pressure of approximately 6 kg/cm$^2$.

2. The process of claim 1, including placing a card carrying data about the plant between the two plastic sheets with the leaf and sealing the card with the leaf.

3. Procedure for the visual and microscopic study of the characteristics of a vegetable plant including the steps of:
    collection and selection of a leaf from the plant;
    submitting of said leaf to a pressing operation at a pressure in a range of approximately 6-7 kg/cm$^2$ to form a pressed leaf;
    drying said pressed leaf at an ambient temperature of approximately 30° C. to form a dried leaf;
    placing said dried leaf in a bath of disinfectant solution to form a disinfected leaf;
    placing said disinfected leaf between two plastic sheets;
    sterilizing said disinfected leaf and plastic sheets at a temperature of approximately 125° C.; and closing said plastic sheets by thermo-welding at a pressure of approximately 6 kg/cm$^2$ and at a temperature of approximately 125° so as to remove air bubbles.

4. Procedure according to claim 3, including the step of inserting, together with the leaf within the plastic a piece of card on which is shown the plant and the characteristics of the same, as well as its applications.

5. Procedure according to claim 3, wherein the plastic is transparent.

* * * * *